United States Patent [19]

Inagi et al.

[11] 4,309,414
[45] Jan. 5, 1982

[54] ANTIINFLAMMATORY ANALGESIC GELLED OINTMENT

[75] Inventors: Toshio Inagi, Hachioji; Toyojiro Muramatsu, Sayama; Hidetaka Nagai, Hachioji, all of Japan

[73] Assignee: Kowa Company Limited, Nagoya, Japan

[21] Appl. No.: 87,574

[22] Filed: Oct. 23, 1979

Related U.S. Application Data

[63] Continuation of Ser. No. 918,021, Jun. 22, 1978, abandoned.

[51] Int. Cl.³ .................. A61K 31/40; A61K 31/78
[52] U.S. Cl. ........................... 424/81; 424/78; 424/274; 424/362; 424/365
[58] Field of Search ............... 424/78, 81, 362, 365, 424/274

[56] References Cited

U.S. PATENT DOCUMENTS

| | | | |
|---|---|---|---|
| 3,640,741 | 2/1972 | Etes | 424/362 X |
| 3,749,773 | 7/1973 | Ninger et al. | 424/81 |
| 3,876,771 | 4/1975 | Denner | 424/78 |
| 3,899,580 | 8/1975 | O'Neill et al. | 424/241 |
| 3,997,482 | 12/1976 | Turkova et al. | 424/78 X |
| 4,013,792 | 3/1977 | Eichman et al. | 424/181 |

FOREIGN PATENT DOCUMENTS 1617653  6/1970  Fed. Rep. of Germany .

OTHER PUBLICATIONS

Merck Index, 9th Ed., 1976, pp. 495 & 505.
Chemical Abstracts, 74: 57306m (1971).
Chemical Abstracts, 83: 72130d (1975).

*Primary Examiner*—Leonard Schenkman
*Attorney, Agent, or Firm*—Oblon, Fisher, Spivak, McClelland & Maier

[57] ABSTRACT

An antiinflammatory analgesic gelled ointment is disclosed which comprises indomethacin, a medium consisting of a glycol, alcohol and water, a gelling agent selected from cellulose and a carboxyvinyl polymer which has been neutralized with an amine, and water sufficiently enough to make up the balance. Such gelled ointment has an excellent antiinflammatory activity.

4 Claims, No Drawings

ANTIINFLAMMATORY ANALGESIC GELLED OINTMENT

This is a continuation of application Ser. No. 918,021, filed June 22, 1978, now abandoned.

BACKGROUND OF THE INVENTION

1. Field of the Invention

This invention relates to an antiinflammatory analgesic gelled ointment containing indomethacin as an active component.

2. Description of the Prior Art

Indomethacin is a compound represented by the formula,

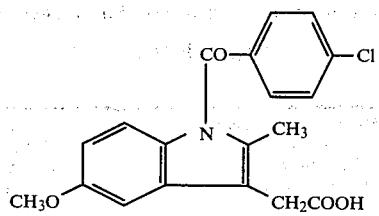

and is well-known as a non-steroid agent having an excellent antiinflammatory activity.

Indomethacin was put on the market in Japan in 1966 in the form of a capsule and has been widely used in the treatment of chronic articular rheumatism, arthritis deformans, inflammatory diseases and inflammation after operation with its prominent effects recognized. The clinical effects of indomethacin are deemed to be the greatest among the currently used non-steroid antiinflammatory agents.

However, the capsule medication of indomethacin induces adverse effects such as gastroenteric disorder due to an oral route, thus giving an impetus to the development of the suppository.

Consequently, the suppository has been used at present together with the capsule in plastic surgery and other fields for purposes of antiinflammation, analgesia and alleviation of fever. The adverse action of indomethacin in terms of gastroenteric disorder is decreased to some extent by the use of the suppository. It is still impossible, however, to administer indomethacin even in the form of a suppository to any patients suffering from peptic ulcer since medication of indomethacin in such form would really result in decreased appetite, nausea, vomiting, stomach ache, diarrhea and lose passage.

In order to overcome the above disadvantageous problem, the present inventors have conducted continuous research to find that the topical application of indomethacin in the form of an ointment produces antiinflammatory analgesic effects to the same extent as attained by the internal use, and completely releases the patients from any adverse reactions caused by the internal medication. Based on this finding, the present invention has been accomplished.

SUMMARY OF THE INVENTION

It is, therefore, an object of the invention to provide an antiinflammatory analgesic ointment containing indomethacin as an active component.

An indomethacin ointment cannot be produced by the conventional method applied to the ointment preparation because indomethacin is only slightly soluble in water and common media. The topical indomethacin suspended in the ointment base is observed to remain unabsorbed by the skin of a human being without any therapeutical effects.

In order to produce an ointment in which indomethacin is dissolved and which can be absorbed easily by the skin of human beings, the present inventors have made a wide variety of studies, and as a result of these studies, they have discovered that indomethacin, which is dissolved in a medium consisting of a glycol, alcohol and water, and which is gelled with a gelling agent, is especially suited to the above purposes, and the absorbed amount is increased by combination with an adjuvant such as diisopropyl adipate, diethyl sebacate, ethyl caproate and ethyl laurate.

Accordingly, this invention provides an ointment comprising indomethacin, a medium consisting of a glycol, alcohol and water, and a gelating agent, and preferably in combination with an adjuvant.

DETAILED DESCRIPTION OF PREFERRED EMBODIMENTS OF THE INVENTION

Suitable glycols useful in the present invention include propylene glycol, butylene glycol, polyethylene glycol and the like. Ethanol and isopropanol are preferably used as suitable alcohols. The combination ranges of 5 to 35% of glycol, 10 to 50% of an alcohol and 30 to 55% of water have been found particularly suitable. By the percents are meant the weight bases throughout the specification.

Suitable gelating agents useful in the invention include a carboxyvinyl polymer and cellulose.

Hydroxyethyl cellulose, methyl cellulose, carboxymethyl cellulose, hydroxypropyl cellulose and the like are used as the cellulose.

The carboxyvinyl polymer previously neutralized with an organic amine such as diisopropanol amine or triethanol amine is used as the gelating agent. This gelating agent is combined preferably in such a way that its final concentration is 0.5 to 5%.

Suitable adjuvants useful in the invention include a $C_1$-$C_5$ alcohol ester of $C_4$-$C_{14}$ monocarboxylic acid and a $C_1$-$C_3$ alcohol diester of $C_4$-$C_{10}$ dicarboxylic acid such as diisopropyl adipate, diethyl sebacate and ethyl caproate. Any one selected adjuvant is preferably combined so that the final concentration may be 0.5 to 5%. Indomethacin is certainly expected to exhibit a sufficient effect in an amount of 0.5 to 1.5%.

The final pH is adjusted from 5.5 to 7.5, preferably from 6.2 to 7.2 since indomethacin is only slightly soluble in an acidic medium, and is so unstable in an alkaline medium as to cause decomposition or degeneration.

For this reason, an antioxidant and antiseptic agent may be added.

The antiinflammatory analgesic gelled ointment according to the present invention can be produced by (1) swelling a gelating agent in water, (2) dissolving indomethacin and an adjuvant in a mixture of a glycol and an alcohol and (3) adding (2) to (1), and further adding an amine to the resulting mixture to form a desired gel ointment.

The thus obtained ointment can resist storage in a stable state for a long period of time and can produce a therapeutically excellent antiinflammatory analgesic effect when applied to a human being by coating, as mentioned hereinafter.

The following examples are set forth in order to further illustrate the invention.

EXAMPLE 1

| | |
|---|---|
| (1) Carboxyvinyl polymer | 1.0 g |
| (2) Indomethacin | 1.0 g |
| (3) Propylene glycol | 10.0 g |
| (4) Ethanol | 40.0 g |
| (5) Diisopropanolamine | 1.1 g |
| (6) Purified water | An amount sufficient to bring the final weight to 100 g |

(A) Swell (1) in 20 g of water.
(B) Dissolve (2) in a mixture of (3) and (4).
(C) Add (B) to (A) and mix until the mixture is completely hydrated.
(D) Dissolve (5) in 10 g of water. Add the mixture to (C) with mixing. Bring the resultant mixture to the final weight with some remaining water and stir the composition until it becomes homogeneous.

EXAMPLE 2

| | |
|---|---|
| (1) Carboxyvinyl polymer | 1.0 g |
| (2) Indomethacin | 1.0 g |
| (3) Propylene glycol | 20.0 g |
| (4) Ethanol | 30.0 g |
| (5) Diisopropanolamine | 1.0 g |
| (6) Purified water | An amount sufficient to bring the final weight to 100 g |

(A) Swell (1) in 20 g of water.
(B) Dissolve (2) in a mixture of (3) and (4).
(C) Add (B) to (A) and mix until the mixture is completely hydrated.
(D) Dissolve (5) in 10 g of water. Add the mixture to (C) with mixing. Bring the resultant mixture to the final weight with some remaining water and stir the composition until it becomes homogeneous.

EXAMPLE 3

| | |
|---|---|
| (1) Carboxyvinyl polymer | 1.0 g |
| (2) Indomethacin | 1.0 g |
| (3) Propylene glycol | 12.0 g |
| (4) Ethanol | 30.0 g |
| (5) Diisopropyl adipate | 2.0 g |
| (6) Diisopropanolamine | 1.1 g |
| (7) Purified water | An amount sufficient to being the final weight to 100 g |

(A) Swell (1) in 20 g of water.
(B) Dissolve (2) in a mixture of (3), (4) and (5).
(C) Add (B) to (A) and mix until the mixture is completely hydrated.
(D) Dissolve (6) in 10 g of water. Add the mixture to (C) with mixing. Bring the resultant mixture to the final weight with some remaining water and stir the composition until it becomes homogeneous.

EXAMPLE 4

| | |
|---|---|
| (1) Carboxyvinyl polymer | 1.0 g |
| (2) Hydroxyethyl cellulose | 1.0 g |
| (3) Indomethacin | 1.0 g |
| (4) Polyethylene glycol 300 | 10.0 g |
| (5) Ethanol | 30.0 g |
| (6) Dissopropyl adipate | 2.0 g |
| (7) Diisopropanolamine | 0.9 g |
| (8) Purified water | An amount sufficient to bring the final weight to 100 g |

(A) Swell (1) and (2) in 20 g of water.
(B) Dissolve (3) in a mixture of (4), (5) and (6).
(C) Add (B) to (A) and mix until the mixture is completely hydrated.
(D) Dissolve (7) in 10 g of water. Add the mixture to (C) with mixing. Bring the resultant mixture to the final weight with some remaining water and stir the composition until it becomes homogeneous.

EXAMPLE 5

| | |
|---|---|
| (1) Hydroxypropyl cellulose | 5.0 g |
| (2) Indomethacin | 0.5 g |
| (3) Propylene glycol | 20.0 g |
| (4) Triethanol amine | 0.35 g |
| (5) Ethanol | 30.0 g |
| (6) Purified water | An amount sufficient to bring the final weight to 100 g |

(A) Swell (1) in 20 g of water.
(B) Dissolve (2) in a mixture of (3) and (5).
(C) Dissolve (4) in the remaining water.
(D) Add (A) and (C) to (B), and stir the resultant mixture until it becomes homogeneous.

EXAMPLE 6

Inhibitory Effect on Carrageenan-induced Edema:

Wister male rats each weighing about 200 g, each group consisting of six rats, were given subcutaneously 0.05 ml of a 1% carrageenan solution on their hind right paws. Immediately, → about 100 mg of the ointment prepared in Example 1 was coated on each injected region which was covered with a polyethylene film and fixed with gauze thereon. Two hours later, the polyethylene film and gauze were removed. One hour after such removal, the weight of edema was measured. The control group was coated only by the ointment base and thereafter treated in the same manner as in the test groups. The results obtained are as shown in Table 1.

TABLE 1

| Agent | Weight of edema (g) Mean ±error | Inhibition ratio (%) |
|---|---|---|
| Control | 0.50 ± 0.03 | — |
| Indomethacin ointment (1%) | 0.35 ± 0.04 | 31.1* |

*$p < 0.05$

EXAMPLE 7

Inhibitory Effect on Acceleration of Blood Vessel Permeability:

Guinea pigs were coated twice with about 50 mg of the ointment prepared as in Example 1 on their hair-removed back skins at an interval of one hour. One hour after a second coating a 1% Evans Blue solution was injected intravenously, and immediately 10 μg of a histamine hydrochloride solution was intradermally injected into each ointment-coated region. 30 minutes later, the animals were depleted to death. Each skin dyed in blue was exfoliated, and the pigment was extracted with pyridine and determined the control group as being coated only by the ointment base and thereafter treated in the same manner as in the test groups.

The results obtained are as shown in Table 2.

TABLE 2

| Agent | Evans' Blue (μg/region) Mean ± error | Inhibition ratio (%) |
| --- | --- | --- |
| Control | 246.2 ± 26.5 | — |
| Indomethacin ointment (1%) | 202.8 ± 28.1 | 17.6 |

EXAMPLE 8

Absorption from Skin:

Guinea pigs were coated with about 1 g of the ointment prepared as in Examples 1 and 3 and suspended with about 0.1 g of the ointment on the back skins each having a region of 2×2 cm from which the hair was removed one day after hair cutting. At the fifth hour after coating, the preparation was recovered and the absorption ratio was calculated from the recovery amount. The result obtained are as shown in Table 3.

TABLE 3

| Test compound | Cream* | ointment in Example 1 | Ointment in Example 3 |
| --- | --- | --- | --- |
| Absorption ratio after 5 hours (%) | 6.0 ± 2.0 | 13.4 ± 2.6 | 25.5 ± 1.1 |

*Prepared according to the method reported in Europ. J. Pharmacol., 3, 157 - (1968)

EXAMPLE 9

The clinical effects of 84 cases collected from three establishments are as shown in Table 4. Parenthesized in this Table are the percentage values.

TABLE 4

| | Excellent | Good | Fair | Ineffective | Aggravation | Unknown | Total |
| --- | --- | --- | --- | --- | --- | --- | --- |
| Distrosion | 1 | 8 | 2 | 2 | 0 | 0 | 13 |
| Contusion | 0 | 7 | 0 | 2 | 0 | 0 | 9 |
| Fracture, dislocation and sequelae | 0 | 2 | 4 | 1 | 0 | 0 | 7 |
| Traumatic arthritis | 0 | 1 | 2 | 1 | 0 | 0 | 4 |
| Total | 1 (3.0) | 18 (54.5) | 8 (24.2) | 6 (18.2) | 0 | 0 | 33 |
| Arthritis deformans | 0 | 3 | 10 | 4 | 0 | 0 | 17 |
| Myositis | 0 | 2 | 0 | 1 | 0 | 0 | 3 |
| Total | 0 | 10 (23.8) | 19 (45.2) | 12 (28.6) | 0 | 1 (2.4) | 42 |
| Swelling post operative | 0 | 3 | 2 | 1 | 0 | 0 | 6 |
| Others | 1 | 0 | 1 | 1 | 0 | 0 | 3 |
| Sum total | 2 (2.4) | 31 (36.9) | 30 (35.7) | 20 (23.8) | 0 | 1 (1.2) | 84 |

What is claimed as intended to be secured by United States letters patent is:

1. An anti-inflammatory analgesic ointment comprising:
indomethacin in the range of from 0.5–1.5% by weight; a medium consisting of a glycol in the range of from 5–35% by weight, an alcohol in the range of from 10–50% by weight, and water in the range of 30–55% by weight and a gelating agent in an amount of 0.5 to 5% by weight selected from the group consisting of a cellulose compound and a carboxyvinyl polymer which has been neutralized with an amine; and adjuvant in the range of from 0.5% to 5% by weight selected from the group consisting of a $C_1$-$C_5$ alcohol ester of a $C_4$-$C_{14}$ monocarboxylic acid and a $C_1$-$C_3$ alcohol diester of a $C_4$-$C_{10}$ dicarboxylic acid; and water in an amount sufficient to make up the balance of the ointment, said ointment being adjusted to the pH of 5.5 to 7.5.

2. The antiinflammatory analgesic ointment according to claim 1, wherein the pH of said ointment is adjusted to within the range of 6.2 to 7.2.

3. The antiinflammatory analgesic ointment according to claim 1, wherein said glycol is selected from the group consisting of propylene glycol, butylene glycol and polyethylene glycol.

4. The antiinflammatory analgesic ointment according to claim 1, wherein said cellulose compound is selected from the group consisting of hydroxyethyl cellulose, methyl cellulose, carboxymethyl cellulose and hydroxypropyl cellulose.

* * * * *